United States Patent [19]

Anthony

[11] Patent Number: 4,533,326

[45] Date of Patent: * Aug. 6, 1985

[54] ORAL PACK RETENTION SYSTEM

[76] Inventor: Albert J. Anthony, 45 Central St., West Boylston, Mass. 01583

[ * ] Notice: The portion of the term of this patent subsequent to Aug. 7, 2001 has been disclaimed.

[21] Appl. No.: 457,762

[22] Filed: Jan. 13, 1983

Related U.S. Application Data

[63] Continuation-in-part of Ser. No. 291,445, Aug. 10, 1981, abandoned.

[51] Int. Cl.³ .............................................. A61C 19/06
[52] U.S. Cl. .................................................... 433/229
[58] Field of Search .................. 128/385, 399, 2, 260, 128/325; 606/1; 633/229, 215, 80; 24/259 R; 604/77

[56] References Cited

U.S. PATENT DOCUMENTS 1,010,146 11/1911 Ivory .
1,730,266 10/1929 Dailey .
2,551,374 5/1951 Hansen .
4,020,558 5/1977 Cournut .

OTHER PUBLICATIONS

P. 572 of Glickman's "Clinical" Periodontology, Recognition, Diagnosis and Treatment of Peridontal Disease in the Practice of General Dentistry, 3rd Edition 1964 (Saunders).
P. 374, Orbon's "Periodontics", 3rd Edition, 1968, C. V. Mosby.
Pp. 744, 746, 747 Glickman's "Clinical Periodontology", 1st Edition, 1953, W. B. Saunders Co.
Pp. 403–405, Journal of Periodontology, vol. 49, Aug. 1978.

Primary Examiner—Robert Peshock
Attorney, Agent, or Firm—Blodgett & Blodgett

[57] ABSTRACT

A system for protecting oral tissue or retaining material at a location within the mouth, consisting of a fixture which is fastened to a tooth and a body of polymeric material cured to the fixture and extending over the tissue or location.

14 Claims, 8 Drawing Figures

ORAL PACK RETENTION SYSTEM

This is a continuation-in-part of application Ser. No. 291,445 filed Aug. 10, 1981, now abandoned.

BACKGROUND OF THE INVENTION

After a dentist has performed one of a variety of types of surgery in the mouth of a patient, it is necessary to protect the surgical site. For that purpose, it is common practice to use a so-called "pack" in the form of an elastomer plastic. Unfortunately, for one reason or another, it is difficult to maintain the pack in place and they tend to become loosened, lost prematurely, and sometimes even swallowed. If this occurs, the surgerized tissue is not protected and the resulting trauma may cause pain, hemorrhage, or susceptibility to infection. A particularly important use for the pack is in the case of the free gingival graft where it is difficult to retain the pack on the donor site on the palate. In that case, it is particularly important to protect the site from which the tissue surface has been removed. Prior to the present invention, the only method of pack retention with any efficiency at all was the "surgical stent" which is a custom-made appliance. These appliances are very time consuming and expensive to make and are relatively uncomfortable for the patient. For these reasons, they are not usually constructed unless very extensive donor sites require dressing (surgical pack). The stent can easily be too lose or too tight, resulting in the loss of the pack. The stent also often allows liquids to seep to the raw tissue causing severe pain. Attempts have been made in the past to provide a means of holding the pack in place, but they have been less than successful, particularly when the wound was located in the palate. These and other difficulties experienced with the prior art devices have been obviated in a novel manner by the present invention.

It is, therefore, an outstanding object of the invention to provide an oral pack retention device to maintain a surgical pack securely in place.

Another object of this invention is the provision of an appliance for periodontal or oral surgical use, where the wound is located on the palate.

Still another object of this invention is the provision of an oral pack system adapted to hold a non-sticking dressing over a wound within the mouth.

An additional object of this invention is the provision of an oral pack system adapted to hold medication in a cavity in the mouth.

A further object of the present invention is the provision of a surgical pack retention device that is adaptable to all positions in the mouth irrespective of the shape, nature, or location of the tooth.

It is another object of the instant invention to provide a periodontal appliance which is simple and rugged in construction, which can be readily manufactured from easily obtainable materials, and which is capable of being sterilized either by autoclave or high dry heat.

It is another object of the instant invention to provide a periodontal appliance which is inexpensive to manufacture and which can be easily applied to either large or small surgical sites.

With these and other objects in view, as will be apparent to those skilled in the art, the invention resides in the combination of parts set forth in the specification and covered by the claims appended hereto.

SUMMARY OF THE INVENTION

In general, the invention consists of a oral pack retention system for use in maintaining a pack in place and having a retention fixture adapted to be located adjacent a tooth. A flexible wire is provided which extend around the tooth and is fastened to the fixture.

Specifically, the fixture has an extruded shape and both the fixture and the wire are formed of stainless steel.

BRIEF DESCRIPTION OF THE DRAWINGS

The character of the invention, however, may be best understood by reference to its structural forms, as illustrated by the accompanying drawings, in which.

DESCRIPTION OF THE PREFERRED EMBODIMENT

Figure 1:
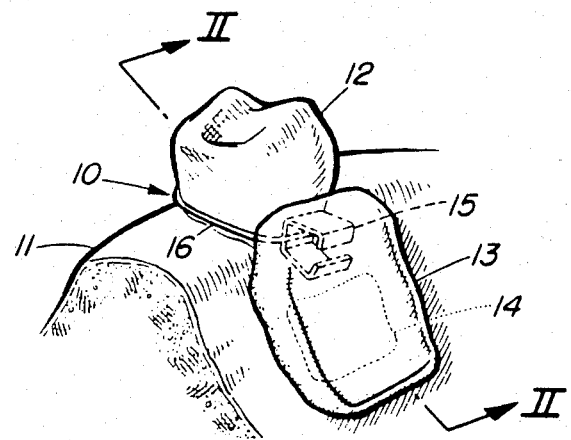
FIG. 1 is a perspective view of a oral pack retention device incorporating the principles of the present invention.

Referring first to FIG. 1, wherein are best shown the general features of one embodiment of the invention, the oral pack retention device, indicated generally by the reference numeral 10, is shown in use in a patient's mouth, having a palatal tissue surface 11 and a tooth 12. The device is shown in use holding a surgical pack 13 over a surgical donor site 14 on the palate 11.

Figure 2:
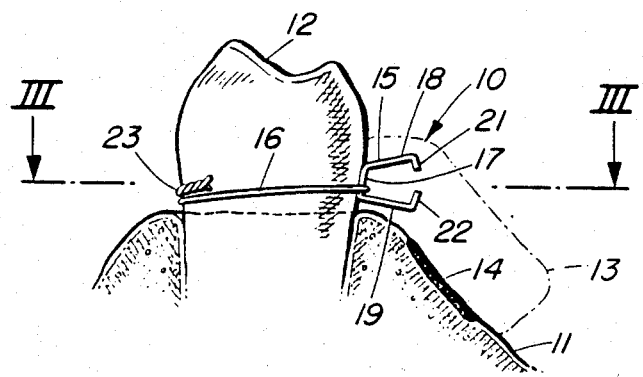
FIG. 2 is a vertical sectional view of the device taken on the line II—II of FIG. 1.
Figure 3:
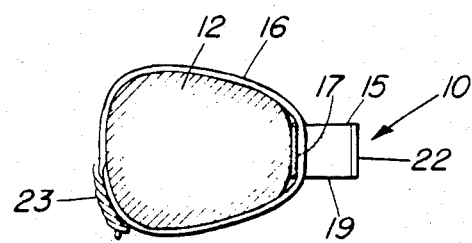
FIG. 3 is a plan view of the device as viewed on the line III—III of FIG. 2.

FIGS. 2 and 3 show the details of the oral pack retention device 10 which has a retention device 15 located adjacent the tooth 12. The device is provided with a wire 16 which extends tightly around the tooth and is fastened to the fixture 15. As is evident in FIG. 2, the fixture 15 has an extruded shape, that is to say, it has a constant cross-section. The wire 16 and the fixture 15 are formed of a non-corrosive material such as stainless steel. The fixture 15 has a flat central portion 17 which lies against the tooth and which is fastened to the wire 16 by welding or the like. The fixture 15 is also provided with arms 18 and 19 which extend laterally away from the central portion 17 at the top and bottom, respectively. These arms extend at an obtuse angle to the central portion. The outer end of the upper arm 18 is provided with a downwardly-extending flange 21, while a similar flange 22 extends upwardly from the outer end of the lower arm 19. The flanges, therefore, extend toward one another to the extent that they each occupy approximately one-third of the space between the ends of the arms.

The method of operation and the advantages of the present invention will now be readily understood in view of the above description. When the surgery (especially a free gingival graft) has been completed, the result is a raw connective tissue area without the normal epithelial covering at the site 14. When the surgery has been completed, it is necessary to apply the pack 14 to protect it and assist in healing. For that purpose, the fixture 15 with the wire 16 attached, is placed against the inner surface of the tooth 12 at a location which is close to where the tooth emerges from the gingiva 11. The ends of the wire 16 are carried around to the outer side of the tooth where they are twisted together to form the portion 23. The portion 23 is then bent back toward the tooth to lie flat against it, so that it does not irritate the portion of the cheek which lies opposite it and would otherwise contact it. The pack 13 is then molded around and within the fixture 15, so that it extends over the site 14. The apparatus holds the pack securely in this way and it is not easily dislodged. This particular manner of holding the surgical pack 13 is particularly adaptable in the case of the free gingival graft, wherein the site 14 is a "donor" site. The invention, therefore, serves the purpose of retaining a periodontal or surgical pack or dressing in the oral cavity subsequent to various types of surgery, especially periodontal surgery. The fixture is anchored firmly to the tooth. The surgical pack material is molded around and within the fixture and against the surface of the tooth to which it is anchored and against adjacent teeth. The pack covers the surgical site and is then allowed to set. This is especially useful at the donor site of a gingival graft which would be on the palate where it is extremely difficult to maintain a pack. The well-retained pack gives post-operative comfort to the patient, protects the tissue from trauma and irritation, and prevents hemorrhage during early healing.

In addition to use in surgical situations, the ease with which this retention system can be installed and the high holding reliability make it practical for retaining medication in desired locations in the mouth. For example, the system has been found effective in retaining anti-bacterial agents in the periodontal pocket at the junction of tooth and gingiva for the required ten days. The system is easy to install and comfortable for the patient.

Figure 4:
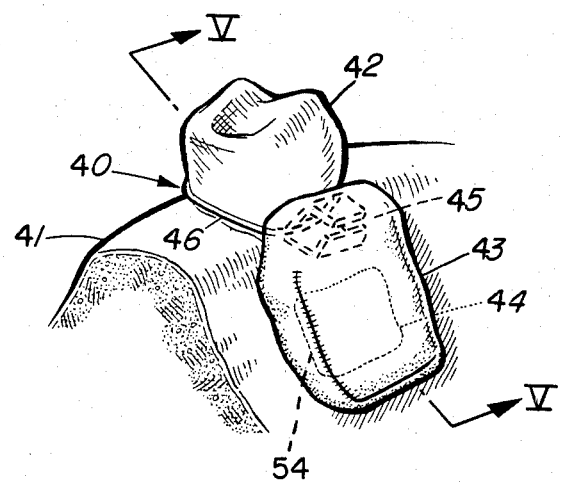
FIG. 4 is a perspective view of another oral pack retention device incorporating the principles of the present invention.

Referring now to FIG. 4, wherein are shown the general features of another embodiment of the invention, the oral pack retention system, indicated generally by the reference numeral 40, is shown in use in a patient's mouth, having a palatal tissue surface 41 and a tooth 42. The device is shown in use in holding a periodontal pack 43 over a surgical donor site 54 on the palate 41.

Figure 5:
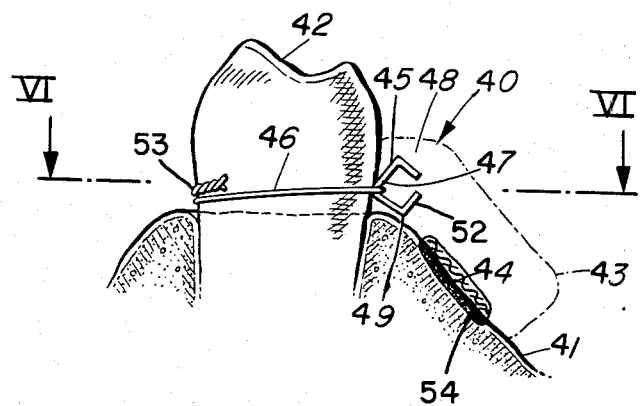
FIG. 5 is a vertical sectional view of the device shown in FIG. 4 taken along the line V—V of FIG. 4.
Figure 6:
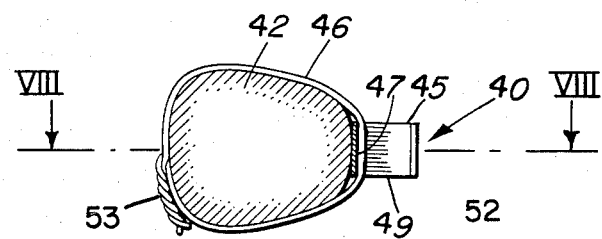
FIG. 6 is a plan view of the device as viewed on line VI—VI of FIG. 5.

FIGS. 5 and 6 show the details of the pack retention system 40 which has a retention device 45 located adjacent the tooth 42. The device is provided with a wire 46 which extends tightly around the tooth and is fastened to the fixture 45. As is evident in FIG. 5, the fixture 45 has an extruded shape, that is to say, it has a constant cross-section. The wire 46 and the fixture 45 are formed of a non-corrosive material such as stainless steel. The fixture 45 has a V-shaped central portion 47 the vertex of which faces the tooth. The fixture is fastened to the wire 46 by welding or the like along the interior of the vertex. The V-shape of the fixture 45 forms arms 48 and 49 which extend divergently away from the apex. The outer end of the upper arm 48 is provided with a downwardly-extending flange 51, while a similar flange 52 extends upwardly from the outer end of the lower arm 49. The flanges, therefore, extend toward one another to the extent that they each occupy approximately one-third of the space between the ends of the arms.

While this embodiment can be used to replace the first embodiment, this embodiment is particularly effective for using a rigid pack to hold a medicated dressing over a surgical wound. As described previously, standard surgical packs are formed of flexible polymers which can be placed in contact with the wound. There are various rigid polymers which are now used for temporary crowns and other applications not involving contact with sensitized tissue. When this rigid polymer is used as a pack, it takes advantage of the rigidity of the mounted fixture and allows substantial distance to exist between the nearest tooth and the wound. In order to allow the rigid polymer to be used, the wound and surrounding tissue are covered with a non-sticking surgical dressing 44 of the type known as Telfa pads. The rigid polymer is cured over the fixture and dressing to form a rigid pack. This rigid pack structure not only provides substantially better protection for the wound against food and tooth brushing, and substantially less irritation to the wound by the pack itself, but also, as stated above, allows the system to effectively protect wounds a significant distance from any tooth.

An additional benefit is that the pads can be filled with medication, which is then delivered to the wound under the pack. It is particularly effective to soak the pad in bovine thrombin, a coagulant that reduces bleeding in a fresh wound.

The V-shape of the fixture allows orientation and positioning of the fixture after the wire has been secured around the tooth. In many situations, the fixture can be set off from the tooth and gingiva. The rigidity of the wire holds the fixture in the desired orientation and position.

Figure 7:
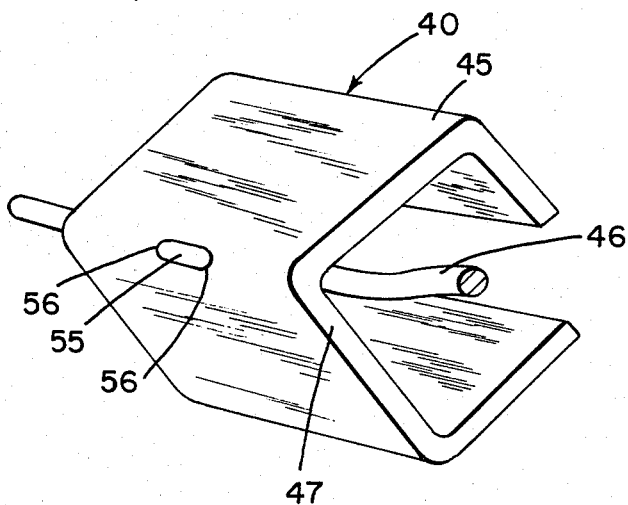
FIG. 7 is a detailed perspective view of the tooth-facing side of the device shown in FIG. 4.

In some situations, however, the shape of the tooth will cause the wire and fixture to tend to slide toward the gingiva. Contact between the fixture and gingiva should be avoided. To eliminate the sliding of the fixture, the tooth-facing side of the fixture is provided with a small scar 55, as shown in FIG. 7.

Figure 8:
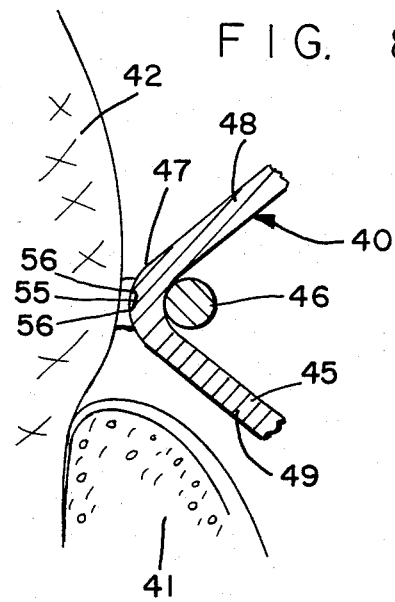
FIG. 8 is a detailed vertical sectional view of the device taken along line VIII—VIII of FIG. 6.

The scar is formed with sharp spines and edges 56. The spines and edges contact the tooth, as shown in FIG. 8, and reduce sliding problems. The scar can be effectively formed by placing the electric welding electrode at the point where the scar is desired when the wire and fixture are welded together.

Another application of this invention concerns the stabilization of teeth that have been reimplanted after traumatic loss or intentional removal during endodontics, that have become mobile, or that have been subject to orthodonic treatment. The invention is also suitable for stabilization of implants, especially of the "blade-vent" type. Standard stabilization techniques are difficult to apply and time consuming. Using the method of the present invention, a fixture is wired, in the manner described above, to each of the subject tooth and the teeth on each side. The uncured "rigid" pack material is applied to form a mass connecting all of the fixtures. The subject tooth is positioned and the pack material is allowed to cure to a rigid form. The resulting structure can remain in place until the tooth is stabilized. The structure can be removed far more easily than the structures resulting from prior techniques, and particularly with less chance of damaging the now stabilized tooth or implant.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. An oral pack retention system for use in covering a location in the mouth, comprising:
   (a) a retention fixture adapted to be located adjacent a tooth,
   (b) a flexible wire adapted to extend tightly around the tooth and to be fastened to the fixture, and
   (c) a mass of pack material cured to the fixture and covering the said location.

2. An oral pack retention system as recited in claim 1, wherein the fixture has an extruded shape, and wherein the fixture and the wire are formed of a corrosion-resistant material.

3. An oral pack retention system as recited in claim 2, wherein the fixture is formed of stainless steel and has a flat central portion that lies along the surface of the tooth and is attached by welding to the wire.

4. An oral pack retention system as recited in claim 3, wherein an arm extends inwardly from the top and bottom of the central portion, each arm lying at an obtuse angle to the central portion, and a flange extends from the end of each arm toward each other.

5. An oral pack retention system as recited in claim 1, wherein a portion of the fixture is formed with a V-shaped cross-section having a vertex and the wire is welded to the interior of the vertex.

6. An oral pack retention system as recited in claim 5, wherein a sharp scar is provided on the exterior of the vertex.

7. An oral pack retention system as recited in claim 1, wherein the fixture has a substantial open three-dimensional shape adapted to anchor effectively in a mass of curable material.

8. An oral pack retention system as recited in claim 1, wherein a non-sticking pad is provided between the pack material and the location.

9. An oral pack retention system as recited in claim 1, wherein the pack material cures to a rigid form.

10. A method for covering a location in the mouth, comprising:
    (a) fixing a fixture, having a wire, to a tooth, by bringing the wire around the tooth, and
    (b) curing a body of curable pack material about the fixture so that the pack material covers the said location.

11. A method as recited in claim 10, wherein the pack material cures to a rigid mass.

12. A method as recited in claim 10, wherein the location is covered with a non-stick pad prior to being covered by the pack material.

13. A method for stabilizing a first periodontal element with respect to a stable peridontal element, comprising the steps of:
    (a) fixing a fixture, having a wire, to the stable element by bringing the wire around the element, and
    (b) curing a body of curable pack material about the fixture and in rigid engagement with said first element.

14. A method as recited in claim 13, wherein the rigid engagement is accomplished by fixing a second fixture to the said first element and curing the pack about the second fixture.

* * * * *